United States Patent
Lachenbruch et al.

(10) Patent No.: US 6,755,852 B2
(45) Date of Patent: Jun. 29, 2004

(54) COOLING BODY WRAP WITH PHASE CHANGE MATERIAL

(76) Inventors: Charles A. Lachenbruch, 126 Linwood La., Summerville, SC (US) 29483; Richard I. Barnett, 921 Prince St., Georgetown, SC (US) 29440

(*) Notice: Subject to any disclaimer, the term of this patent is extended or adjusted under 35 U.S.C. 154(b) by 0 days.

(21) Appl. No.: 10/013,442

(22) Filed: Dec. 8, 2001

(65) Prior Publication Data

US 2003/0109911 A1 Jun. 12, 2003

(51) Int. Cl.[7] ................................. A61F 7/00
(52) U.S. Cl. ................... 607/114; 607/96; 607/112; 607/108
(58) Field of Search ................... 607/96, 108, 109, 607/110, 111, 112, 114

(56) References Cited

U.S. PATENT DOCUMENTS

| | | | |
|---|---|---|---|
| 3,313,405 A | 4/1967 | Blackford | |
| 4,391,267 A | 7/1983 | Arrhenius | |
| 4,596,250 A * | 6/1986 | Beisang et al. | 607/114 |
| 4,667,658 A | 5/1987 | Guibert | |
| 4,671,267 A | 6/1987 | Stout | |
| 4,708,812 A | 11/1987 | Hatfield | |
| 4,756,299 A | 7/1988 | Podella | |
| 4,914,717 A | 4/1990 | Gibbon | |
| 4,964,402 A * | 10/1990 | Grim et al. | 607/111 |
| 4,981,135 A * | 1/1991 | Hardy | 607/108 |
| 5,069,208 A * | 12/1991 | Noppel et al. | 607/114 |
| 5,072,455 A | 12/1991 | St. Ours | |
| 5,088,487 A | 2/1992 | Turner | |
| 5,094,238 A | 3/1992 | Gibbon | |
| 5,098,621 A | 3/1992 | Hermann | |
| 5,190,031 A | 3/1993 | Guibert et al. | |
| 5,211,949 A * | 5/1993 | Salyer | 607/108 |
| 5,275,156 A | 1/1994 | Milligan et al. | |
| 5,277,180 A | 1/1994 | Angelillo et al. | |
| 5,290,904 A | 3/1994 | Colvin et al. | |
| 5,334,646 A | 8/1994 | Chen | |
| 5,366,801 A | 11/1994 | Bryant et al. | |
| 5,431,622 A | 7/1995 | Pyrozyk et al. | |
| 5,443,487 A | 8/1995 | Guibert et al. | |
| 5,456,704 A | 10/1995 | Kilcullen | |
| 5,456,852 A | 10/1995 | Isiguro | |
| 5,486,207 A | 1/1996 | Mahawili | |
| 5,575,815 A | 11/1996 | Slepian et al. | |
| 5,630,961 A | 5/1997 | Salee | |
| 5,637,389 A | 6/1997 | Colvin et al. | |
| 5,702,375 A | 12/1997 | Angelillo et al. | |
| 5,713,143 A * | 2/1998 | Kendall | 36/145 |
| 5,722,482 A | 3/1998 | Buckley | |
| 5,737,774 A | 4/1998 | Petty-Saphon et al. | |
| 5,750,962 A | 5/1998 | Hyatt | |
| 5,887,437 A | 3/1999 | Maxim | |
| 5,932,129 A | 8/1999 | Hyatt | |
| 5,984,953 A * | 11/1999 | Sabin et al. | 607/114 |
| 5,993,480 A | 11/1999 | Burrows | |

(List continued on next page.)

OTHER PUBLICATIONS

U.S. patent application Ser. No. 10/013,419, Lachenbruch et al., filed Dec. 8, 2001.

(List continued on next page.)

*Primary Examiner*—Linda C. M. Dvorak
*Assistant Examiner*—Jocelyn Ram
(74) *Attorney, Agent, or Firm*—Kathleen M. Harleston; Harleston Law Firm LLC

(57) ABSTRACT

A cooling body wrap for rapidly inducing hypothermia, includes: (a) a fluid-impermeable, flexible, conformable envelope; (b) a mixture of from about 20 to about 90 weight % of alkanes having a carbon chain length of between 10 and 14, and from about 10 to about 80 weight % of a gel or viscous fluid carrier in which the alkanes are relatively evenly distributed, the mixture being sealed within the envelope; (c) at least one layer of insulation adjacent to a first side of the envelope; and (d) fastening means for fastening the body wrap around a body part.

20 Claims, 2 Drawing Sheets

U.S. PATENT DOCUMENTS

| | | | |
|---|---|---|---|
| 6,004,662 A | | 12/1999 | Buckley |
| 6,007,572 A | | 12/1999 | Baldwin |
| 6,083,254 A | * | 7/2000 | Evans .......................... 607/96 |
| 6,099,894 A | | 8/2000 | Holman |
| 6,120,530 A | * | 9/2000 | Nuckols et al. ............. 607/108 |
| 6,132,455 A | | 10/2000 | Shang |
| 6,179,879 B1 | | 1/2001 | Robinson et al. |
| 6,183,855 B1 | | 2/2001 | Buckley |

OTHER PUBLICATIONS

U.S. patent application Ser. No. 10/013,443, Lachenbruch et al., filed Dec. 8, 2001.

U.S. patent application Ser. No. 10/012,772, Lachenbruch et al., filed Dec. 8, 2001.

Lon R. Horwitz, DPM, CWS; Thomas J. Burke, PHD: and Dale Carnegie, DPM, Augmentation of Wound Healing Using Monochromatic Infrared Energy, Advances in Wound Care, Jan./Feb. 1999, pp. 35–40, vol. 12 No. 1, Denver, Colorado, USA.

David P. Colvin, Enhanced Thermal Management Using Encapsulated Phase Change Materials an Overview, Advances in Heat and Mass Transfer in Biotechnology, ASME, 1999, HTD–vol. 363/BED–vol. 44, USA.

Mark E. Holman, The Use of Microencapsulated Phase–Change Materials to Enhance the Thermal Performance of Apparel, Advance in Heat and Mass Transfer in Biotechnology, 1999, pp. 235–239, HTD–vol. 363/BEDvol. 44 ASME, USA.

Perry S. Tepperman, MD, and Michael Devlin, MD, Therapeutic Heat and Cold, Postgraduate Medicine, Jan. 1983, pp. 69–76, vol. 73/No. 1, USA.

Justus F. Lehmann, M.D., C. Gerald Warren, M.P.A., and Stewart M. Scham, M.D., Therapeutic Heat and Cold, Clinical Orthopaedics and Related Research, pp. 207–245, USA.

Michael Sawyer, P.T., and Candise K. Zbieranek, P.T., The Treatment of Soft Tissue After Spinal Injury, Clinics in Sports Medicine, Apr. 1986, pp. 387–405, vol. 5, No. 2, Long Beach, California, USA.

Linda J. Hayes, Fabric With Micro Encapsulated Phase Change, Advances in Bioheat and Mass Transfer: Microscale Anaylsis of Thermal Injury Processes Instrumentation, Modeling, and Clinical Application, ASME, 1993, pp. 47–52, HTD–vol. 268, USA.

Phase–Change Heat–Storage Module, NASA Tech Briefs, Apr. 1989, p. 103, USA.

J. C. Mulligan, D. P. Colvin and Y. G. Bryant, Use of Two–Component Fluids of Microencapsulated Phase–Change Materials for Heat Transfer in Spacecraft Thermal Systems, Jun. 20–23, 1994, pp. 1–10, AIAA 94–2004, American Institute of Aeronautics and Astronautics, Washington, DC, USA.

D. P. Colvin, J. C. Mulligan, and Y. G. Bryant, Enhanced Heat Transport in Environmental Systems Using Microencapsulated Phase Change Materials, Jul. 13–16, 1992, 921224, SAE The Engineering Society for Advancing Mobility Land Sea Air and Space International, Warrendale, PA, USA.

Flam, E., Isayeva, E., Kipervas, Y., Shklyarevsky, V., and Raab, L. (1995). Skin Temperature and Moisture Management with a Low Air–Loss Surface. Ostomy Wound Management 41(9).

Kloth, L.C., Berman, J.E., Minkel, S., Sutton, C.H., Papanek, P.E., and Wurzel, J. (2000). Effects of Normothermic Dressing on Pressure Ulcer Healing. Advances in Skin & Wound Care, 13(2).

Price, P., Bale, S., Cook, H., and Harding, K.G. (2000). The Effect of a Radiant Heat Dressing on Pressure Ulcers. J. Wound Care, 9(4).

Microencapsulated Phase–Change Materials for Storage of Heat, NASA Tech Briefs, Jul. 1989, USA.

Santilli, S.M., MD, Ph.D., Valusek, B.A., Robinson C., BSN, RN, CVN, Use of a Noncontact Radiant Heat Bandage for the Treatment of Chronic Venous Stasis Ulcers. Advances in Wound Care, Mar. 1999, 13(2).

* cited by examiner

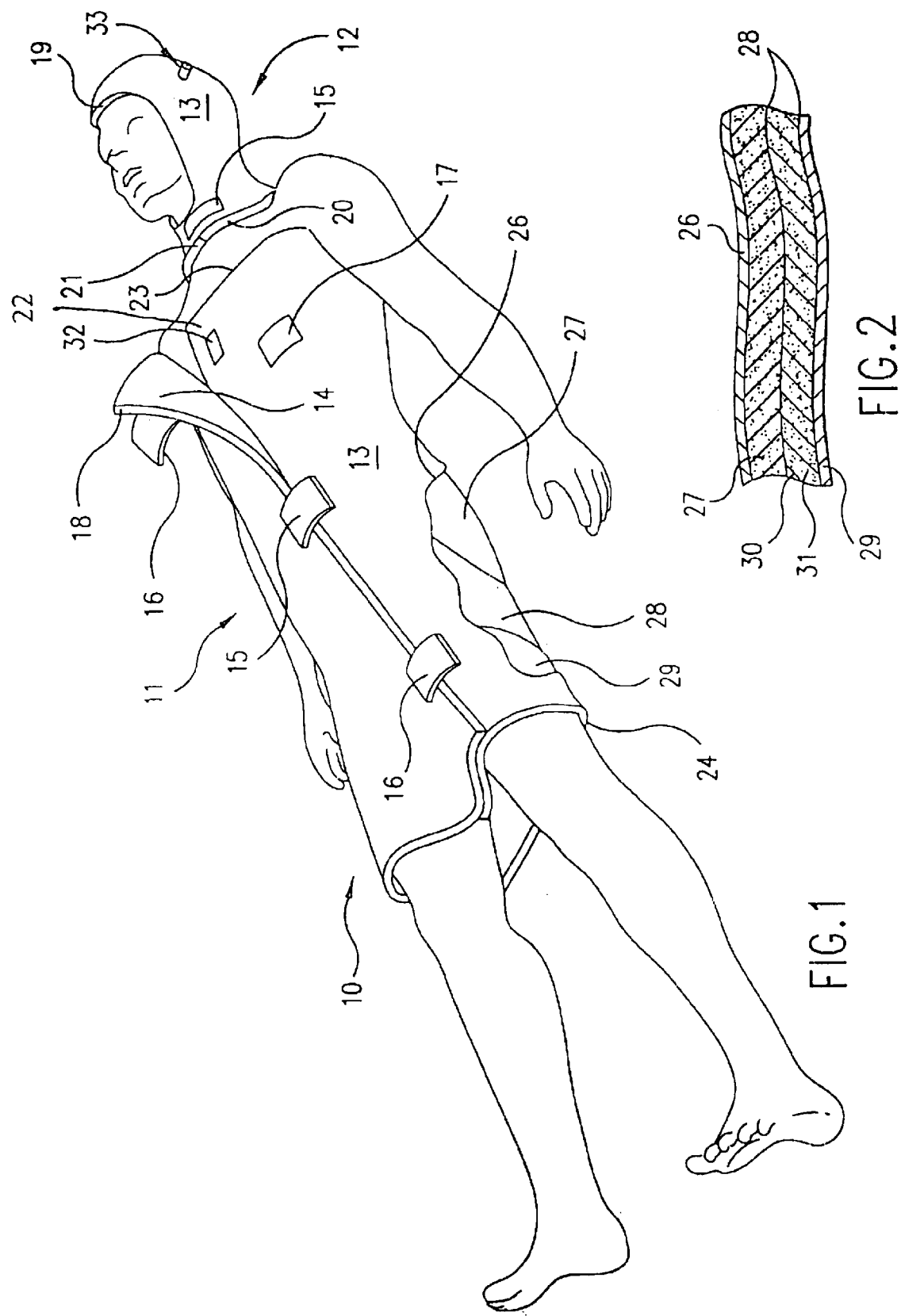

COOLING BODY WRAP WITH PHASE CHANGE MATERIAL

BACKGROUND OF THE INVENTION

1. Technical Field

The present device is an unpowered body wrap containing phase change material with a melting point of between about −10 and 6 degrees Centigrade, the phase change material being distributed in a gel or viscous fluid carrier, for quick, thorough cooling of a portion of the body in the event of a stroke, heart attack, or other emergency medical condition.

2. Background Information

Rapid response is vital in the emergency treatment of strokes and heart attacks. Medical experts are finding that immediately inducing a state of hypothermia in stroke victims, for example, along with administering certain intravenous medications, ameliorates damage from a stroke. Many of the adverse effects of a stroke occur within the first few hours of the actual stroke, which is caused by blockage of a blood vessel by a blood clot. In the hypothermic state, the stroke victim's metabolic rate is reduced, which in turn reduces the adverse after-effects of the stroke, and even cheats death in some cases. To be effective, hypothermia should be induced as rapidly as possible. Quick treatment is imperative. The adverse effects of stroke include impaired motion on one side of the body, short-term memory loss, slurred speech, confusion, etc. Strokes occur spontaneously in teens and adults of any age, although they occur more frequently in older people. It is a leading cause of long-term disability and death in Americans over age 45. Rapidly reducing body temperature is also known to be helpful in treating heart attacks, head injuries, and limb amputations, and may prove to be helpful for treating other types of injuries. Cardiovascular disease is the most significant health problem in the United States today, afflicting roughly one quarter of adult Americans. If rapid body temperature reduction can be done safely by emergency personnel in the field, more patients can be saved and/or have an improved prognosis.

There is a need for an inexpensive, easy to use, portable device which can be used in the field and elsewhere to quickly drop body temperature. Ice packs rapidly lower body temperature, but they are difficult to keep in place on a patient, particularly one who is being jostled in a moving ambulance. One ice pack only covers a small area of the body. Also, most frozen ice packs do not conform easily to the shape of the body part.

The present invention is an unpowered, portable, quick cooling body wrap that can be cooled in a freezer or by any other suitable means of cooling, optionally stored in a cooler, and then quickly wrapped around the torso or other affected body part of the patient to rapidly reduce core body temperature. The body wrap of the present invention is lightweight, inexpensive, and easily conforms to the shape of the body. It can be stored in a cooler in an ambulance, for example, and used in the field. The body wrap, or "cocoon", stays cool for a sustained period. It retains its cooling effect long enough to be stored in a cooler, and/or to reduce and maintain the low body temperature during the ambulance ride to the hospital, for example. It is flexible and easy to use, and even an untrained person, such as a patient's spouse or a nursing home aide, can wrap it around an injured person, once they are directed to do so by a medically trained person.

Cooling of the skin is accomplished in the present invention by means of an envelope containing specific phase change materials (PCMs) distributed in a gel or viscous fluid carrier. The use of phase change materials also ensures that the cold temperatures are delivered to the skin in a precisely selected temperature range that has been found to induce hypothermia. That selected temperature range is the phase change temperature, or melting point of the phase change material.

BRIEF SUMMARY OF THE INVENTION

The present invention provides a body wrap for rapidly cooling a part of the body, including:

(a) phase change material having a melting point of between about −10 and 6 degrees Centigrade;

(b) a gel or viscous fluid carrier in which the phase change material is substantially evenly distributed;

(c) a fluid-impermeable, conformable envelope surrounding the phase change material and the carrier;

(d) fastener means for removably fastening the body wrap around the body part; and (e) at least one layer of insulation adjacent to the envelope.

The invention also includes a cooling body wrap for rapidly inducing hypothermia in a human body, comprising:

(a) a fluid-impermeable, flexible, conformable envelope;

(b) a mixture of from about 20 to about 90 weight % of alkanes having a carbon chain length of between 10 and 14, and from about 10 to about 80 weight % of a gel or viscous fluid carrier in which the alkanes are substantially evenly distributed, the mixture being sealed within the envelope;

(c) at least one layer of insulation adjacent to a first side of the envelope; and (d) fastening means for fastening the body wrap around a part of the body. A preferred fifth element is a heat tube layer adjacent to an opposite, second side of the envelope, the heat tube layer being comprised of a plurality of heat tubes connected to one another.

BRIEF DESCRIPTION OF THE SEVERAL VIEWS OF THE DRAWINGS

A more complete understanding of the invention and its advantages will be apparent from the following detailed description taken in conjunction with the accompanying drawings, wherein examples of the invention are shown, and wherein:

FIG. 1 shows a perspective view of a body wrap according to the present invention, including a cutaway view of the interior;

FIG. 2 is a cross-sectional view of the body wrap according to FIG. 1;

DETAILED DESCRIPTION OF THE INVENTION

Figure 3:
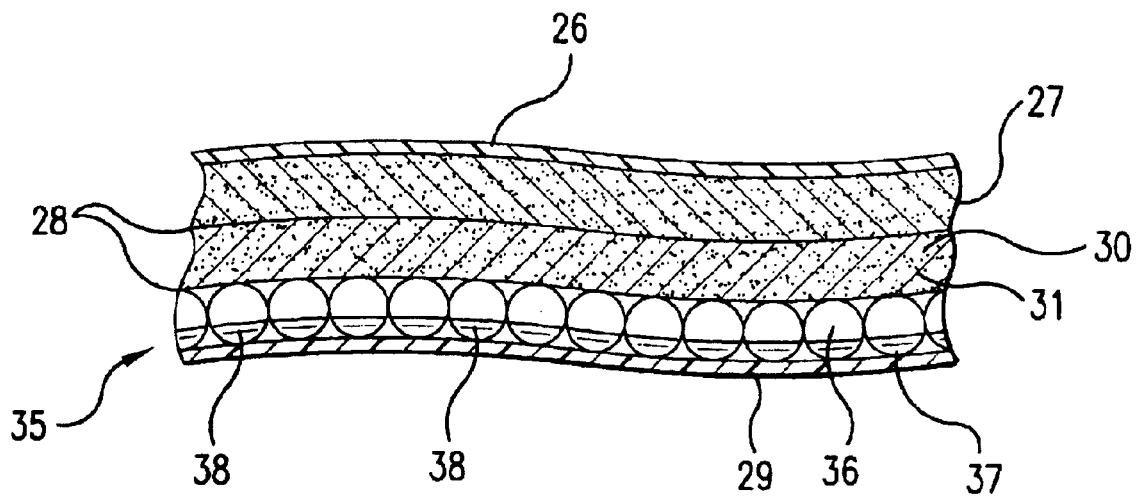
FIG. 3 is an alternative cross-sectional view of the body wrap according to FIG. 1.

In the following description, like reference characters designate like or corresponding parts throughout the several views. Also, in the following description, it is to be understood that such terms as "inside," "outside," "within," and the like are words of convenience and are not to be construed as limiting terms. Referring in more detail to the drawings, the invention will now be described.

Turning first to FIG. 1, a body wrap, generally referred to as 10, according to the present invention includes a cutaway portion along the side for purposes of illustration. There are various embodiments of the body wrap 10 herein. In FIG. 1, a torso body wrap 11 and a head body wrap 12 are illustrated on a patient. The body wrap 10 has an outside face 13 facing outward, and an inside face 14 facing toward the patient. In use, the torso body wrap 11 is wrapped around a patient's torso in order to rapidly induce hypothermia. This device allows a nonprofessional to induce hypothermia in a non-invasive manner in a patient who has just had or is having a heart attack or stroke or any other injury for which hypothermia is indicated. The torso body wrap 11 is generally rectangular in shape, with fastening means 15 attached to the body wrap on its outside face 13.

As shown in FIG. 1, the fastening means 15 includes a number of first fastening members 16 attached along a first side 18 of the body wrap, and a corresponding number of complementary second fastening members 17. The preferred fastening means is hook and loop strips, which are comfortable to lie on, in the event that a hook and loop strip ends up on the part of the body wrap under the body, and do not interfere with rolling or folding the body wrap. The body wrap 10 can be rolled up for storage in the freezer or cooler, for example, and for transport. There are optionally several rows of corresponding fastening means 17 attached to the outside face of the body wrap, so that the body wrap accommodates thin, medium, or stout men and women of varying statures. The body wrap can be bound tightly around the torso or other body part where pressure on a gut wound, for example, is advantageous. In its preferred embodiment, the body wrap 10 is one piece.

As shown in FIG. 1, the head body wrap 12 snugly encloses the patient's head from the top of his head to his collarbone, with a cutout 19 for his face. The head body wrap fastener means 15 fastens a left neck flap 20 to a right neck flap 21 of the head body wrap under the patient's chin, leaving only the patient's face exposed. The head body wrap is used to treat certain types of head injuries, such as a head wound, or a stroke. Chilling the body several degrees in this manner is believed to limit the adverse effects from a stroke and improves the chances that the patient will fully recover. The head body wrap 12 can be used in conjunction with the torso body wrap 11. It is easily slipped over the patient's head and fastened around his neck. Smaller or larger body wraps are also included herein, such as a full body wrap, or appropriately sized body wraps for the arm, leg, neck, and finger. One or more body wraps can be used on the same patient at the same time, depending upon the condition being treated.

To use the torso body wrap 11, the paramedic or other caregiver preferably rolls the first side 18 of the flexible body wrap inward about one third to one half of the width of the wrap, and pushes the roll under the prone or supine patient. This is somewhat similar to the way a clean bedsheet is put on a hospital bed under a prone or supine patient. The patient is then tipped slightly upward from the opposite side while the caregiver grasps the rolled side under the patient and unrolls it toward himself. Minimal movement of the patient is involved. The opposite, second side 22 of the body wrap 11 is then flipped over the top of the patient, and the first side 18 is flipped over the outside face 13 of the second side 22. It is preferred that one or more of the fasteners 15 then be fastened to minimize exposure of the patient's skin to the environment and maintain a cold "cocoon" around the patient. The patient's arms may be wrapped within the body wrap, too, though the top edge 23 of the torso body wrap 11 preferably fits up into the patient's armpits, leaving the arms free. The bottom edge 24 of the torso body wrap preferably falls along an upper portion of the legs.

The body wrap 10 is lightweight, durable, washable, easy to use, inexpensive to make, and reusable. It is usable in the field, operating room, nursing home, or even in the home of a person with a history of strokes or heart attacks. The body wrap 10 can also be used on patients in chiropractic offices or sports therapy clinics for treating musculoskeletal injuries. It can be used to temporarily reduce the severity of essential tremors in the arms, for example. It can be included in First Aid kits built for situations where these types of injuries are likely. It can be stored in a conventional or specialized cooler on a helicopter, for example, and dropped with other supplies for use by medics on the battlefield or at a field hospital pending airlift to a fully equipped hospital, or it could be used for temporarily preserving a corpse. The body wrap 10 can be used anytime and anywhere very cold temperature is desired.

If desired, the body wrap 10 can be cut down to a smaller size prior to use. A full size torso body wrap 11 can be marked with patterns for limb-sized body wraps, for example. Then the full sized wrap can be cut down to the desired size with scissors in the field. Fastening means can be located in appropriate places on the body wrap for closing the different sized wraps within the full sized wrap, particularly hook and loop strips, which do not interfere with operation of the body wrap.

As indicated in the cutaway of FIG. 1 and the cross-section of FIG. 2, the body wrap 10 is comprised of at least two, and preferably four, layers: 1) an optional outer protective layer 26, preferably of nylon material or the like; 2) at least one layer of insulation 27; 3) a PCM-containing envelope 28 adjacent to the insulation layer 27; and 4) an optional inner, conformable layer 29, preferably made of nylon or the like. The inner and outer layers 29, 26 and the insulation layer 27 are conformable to the body and the flexible envelope 28, which is also conformable to the body. The inner layer 29 is made of a nonallergenic, comfortable material capable of being worn against the skin for hours. The envelope 28 is preferably sandwiched between two layers of insulation 27, so that the frozen envelope does not lie directly on the patient's skin. In addition to cushioning, the insulation layer 27 also prolongs the cold temperatures, hence the effectiveness, of the envelope 28.

Continuing to refer to FIGS. 1 and 2, the envelope 28 in the body wrap 10 holds a gel or viscous fluid carrier 30 in which phase change material 31 is substantially evenly distributed. Gel and fluid carriers with a viscosity of more than about 5 centipoise are more preferred, and it is believed that a gel carrier is optimal for maintaining phase change material distribution in the envelope 28. The carrier and phase change material are both preferably non-toxic, in case of a leak in the envelope.

For body wraps herein, the phase change material 31 has a melting point, or phase change temperature, of between about −10 and 6 degrees Centigrade. The phase change material is one that is capable of being suspended in the gel or viscous fluid carrier herein. Phase change materials for use in a body wrap of the present invention have a phase change such that temperatures of the skin area covered will be brought to between about 15 and 27 degrees Centigrade. The normal core temperature ("normothermia") of the human body is between about 36° and 38° C. Skin temperature typically ranges between about 31° C. and about 38° C.

To use the body wrap 10, it is cooled in a freezer, or refrigerator, or by other cooling means at a temperature cool enough to cause solidification of a majority of the included phase change material after about 20 to 60 minutes in the freezer. The body wrap 10 can then be stored in a cooler before being wrapped around the body part. The body wrap can only be stored in the cooler for a finite period, depending upon the phase change temperature of the phase change material 31 and the cooling capacity of the cooler. The body wrap 10 cannot be stored indefinitely in the cooler; it must be refrozen to drop the temperature back down to phase change if it is allowed to warm for too long. The body wrap 10 can be frozen and allowed to warm back to room temperature many times over many years, without a discernable dropoff in efficacy. It can be stored at room temperature for long periods. It is preferably washable, although it is also inexpensive enough for a layperson to be able to afford a replacement if disposal is desired.

By maintaining the body temperature at a level sufficient to induce hypothermia, the body metabolism is significantly lowered, resulting in fewer adverse effects from the condition being treated. The body wrap will then maintain the temperature within the prescribed range for a predictable period of time. In other words, the body wrap 10 will ordinarily maintain the low body temperature until the patient can be transported to an operating room or a fully equipped emergency room, for example.

The viscous fluid or gel carrier 30 in which the phase change material 31 may be suspended is contained within the thin, fluid impermeable, conformable envelope 28. The concentration of phase change material 31 to carrier 30 by weight is preferably between about 1:4 and 4:1 (most preferably about 60 PCM: 40 carrier). This ratio has generally been found to be of importance because, for most types of phase change materials and carriers, the more phase change material that is added to the carrier beyond a certain minimal level, the stiffer and firmer the mixture becomes. Although in general more phase change material means better and longer cooling, too much phase change material has been found to produce an overly bulky, unacceptably rigid envelope. The body wraps of the present invention are relatively thin and flexible, despite the phase change material 31 and carrier 30 in the envelope.

Without meaning to be bound by theory, it is believed that leaving about ¼ of the phase change material unmelted ensures that the body wrap 10 will not be overcooled when it is cooled by dry ice. As long as some phase change material remains in the opposite state, the temperature of the envelope 28 will not exceed its phase change temperature.

Phase change materials are normally classified according to their melting points. Since most phase change materials are not pure, they melt over a range of one or two degrees of temperature. When they are frozen to a temperature within the specified temperature range, the bulk of the liquid phase change materials within the phase change material mixture will solidify. Many variables contribute to the performance of the body wrap, including the type of phase change material and carrier, whether the phase change material is encapsulated, how long it is cooled, the size of the body wrap 10, and the body temperature, lean body mass, and subcutaneous fat level of the patient on whom the body wrap is applied. As the phase change material provides cold temperatures to the skin below the envelope. Because the phase change material's phase change occurs at a specific temperature, the cold is only delivered at this specific temperature, or slightly more than it, depending upon the thickness of the insulation between the PCM-containing envelope 28 and the wrapped area of the body. This makes it ideal for temperature-controlled application of cold temperatures.

In general, the cold phase change material 31 cools the carrier 30, which cools the envelope 28, which cools the insulation layer 27, which lowers the patient's skin temperature and ultimately, with sustained application over a broad area, induces hypothermia. Preferably, once the phase change material 31 is cold, the body wrap 10 cools the user's skin to between about 15 and 27 degrees Centigrade for between about 30 minutes and four hours. The temperature of the carrier and the phase change material suspended in it must be a few degrees colder than this in order to drive cold temperature toward the body. Some cold will be lost to the environment once the body wrap 10 is wrapped around the user's body, but the rate of warming from the environment will be reduced by the outer insulation layer.

Suitable phase change materials for cooling applications herein include C12 to C14 alkanes (i.e., alkanes with between about 12 and 14 carbons), and mixtures thereof. Preferred alkanes for use herein, then, are dodecane (C12), tridecane (C13), and tetradecane (C14). The alkanes used in this invention can be varied according to the degree of cooling necessary for the particular part of the body on which the body wrap 10 will be used, the length of time that cooling is desired, or the patient's particular condition (stroke, heart attack, etc.). Alkanes may be selected according to the degree of cooling necessary to achieve the desired cooling effect. Alkanes may also be selected and mixed based on budget constraints, since some of them are more expensive than others.

Phase change material 31 for use herein is preferably microencapsulated so that it remains evenly distributed throughout the carrier 30 even after many cooling/warming cycles. This is important because many phase change materials, such as the alkanes, are by themselves poor thermal conductors. Alkanes are also hard, waxy, and not conformable in the solid state. The distribution of the phase change material into small, generally spherical capsules with a diameter of between about one and 100 microns significantly enhances heat transfer between the surrounding medium and the phase change material. It also allows the mass to conform to the body as the liquid or gel carrier between capsules allows them to slide relative to one another despite the fact that the frozen PCM itself is rigid. Microencapsulation also prevents interaction, chemical or otherwise, over time between the phase change material and the carrier or envelope material, thus increasing product durability. Any suitable method for encapsulating the phase change material in a protective coating can be utilized. Powder phase change material is preferably used because it is believed to have good conductivity due to its higher surface area and distributes well into a conformable PCM/carrier mixture. The phase change materials are preferably microencapsulated in a thin coating, more preferably a polymer. The coating preferably forms a generally spherical shell around the phase change material with a preferred shell thickness of between about 0.003 and two microns, most preferably about 0.05 micron.

The body wraps 10 herein are not powered and do not comprise a power source. Since the body wrap is pre-cooled, it does not have to be attached to an electrical source or batteries while it is on the patient, nor is control circuitry necessary in order for the envelope 28 to remain cold for the specific period of time. The body wrap 10 does not include a microprocessor, EEPROM, or the like.

Prior to using the body wrap 10, it is placed in a freezer to cool. Other means of cooling, such as refrigeration or dry ice, may be employed. Special care should be taken at the lower end of the temperature range (−10 degrees C.) because an uninsulated envelope 28 could conceivably harm a patient's skin.

As shown in FIG. 1, a visible temperature indicator is preferably included on the body wrap 10 so the paramedic or other caregiver knows when to remove it from the freezer. When cooled, the body wrap will cool to the temperature of phase change according to the phase change material used in that body wrap. The body wrap can be used immediately or stored in a freezer for use in the field. The body wrap 10 is removed from the cooler and wrapped around the torso or other involved part of the body, to cool the part down quickly and thoroughly.

Various systems can be used for determining when the body wrap 10 is cooled to the appropriate degree. The simplest and most preferred system is to keep the body wrap in a freezer that is set to approximately five degrees cooler than the phase change temperature. After about 20 minutes in the freezer, the body wrap is ready for immediate use as needed. Another system utilizes a small thermal window 32 or slit on the outer face 13 of the body wrap 10. A color-coded window may be included on the body wrap, or on a wrapper around it. The thermal window 32 allows the user to view a thermal indicator placed inside the body wrap, which senses the temperature of the envelope 28. The thermal indicator changes in some visible way, such as a color change, to indicate to the user that the PCM-containing carrier has been cooled to the pre-determined temperature. This system is inexpensive because a conventional freezer can be employed. A color-coded temperature indicator may also be applied directly on the inside or outside faces of the body wrap.

Another way for the user to determine when the body wrap is properly chilled is a thermometer 33, as shown on the head body wrap 12 in FIG. 1. The lower end of the thermometer rests inside the body wrap, preferably in, on or very near the envelope 28. When the pre-determined temperature is reached, the body wrap 12 can be removed from the freezer and used.

The fluidic PCM/carrier contents are enclosed by the flexible envelope 28, which is then preferably heat sealed along its edges. In a preferred embodiment, the envelope 28 is urethane film, the carrier 30 is a silicone fluid, and the phase change material 31 is C12 and C14 alkane encapsulated into microcapsules having a diameter between about one and 100 microns. The envelope 28 is preferably made of a urethane film with a thickness of between about 0.003 and 0.08 inch. The shape and size of the envelope may be varied. The envelope 28 itself is preferably between about 0.1 and 1.5 inches thick, most preferably one inch thick. The envelope 28 may include internal divisions to isolate PCM microcapsules into pockets. The body wrap 10 and/or envelope 28 may, for example, be quilted, with a small amount of phase change material and carrier in each quilt square. The body wrap 10 is preferably between about 0.5 and five inches thick, more preferably between about one and two inches thick.

The PCM-containing envelope is preferably sandwiched between the conformable thermal insulation layers 27, which are preferably made of thin sheets of hollow fiber polymer, or any other suitable insulative, soft, cushioning, comfortable, absorbent, conformable material. The primary function of the insulation layer is to limit the escape of cold from the envelope, and protect the skin from the cold temperatures.

The phase change material is substantially evenly distributed in the carrier 30 which is a gel, such as a urethane gel or a viscous fluid. By "viscous fluid" is meant a fluid with an absolute viscosity between about five and about 100,000 centipoise, most preferably between about five and about 10,000 centipoise. Generally, the carrier stiffens as phase change material is added. Carriers 30 with a lower viscosity are preferable herein because the envelope 28 will be soft and flexible. Urethane gels, silicone fluids, and mineral oils are among the suitable carriers in this regard. It is also believed that inexpensive oils, such as vegetable oil, olive oil, or peanut oil, may also be employed herein, so long as they have a suitably high viscosity and a preservative is included. The carrier 30 and phase change material 31 are both preferably non-toxic, and mixable. The phase change material must maintain distribution within the carrier through many cold/warm cycles. The viscous, conformable fluid carrier herein should be one that does not foster bacterial or fungal growth when confined in the air- and fluid-impermeable envelope.

It is believed that a viscous fluid is optimal herein for maintaining phase change material distribution and for even cooling. Viscosity is a significant property of the material that is selected to carry the phase change material because it determines, in large part, the conformability of the PCM/carrier mixture and the extent to which an even distribution can be maintained over many use cycles. Viscosity is basically the resistance to change of form exhibited by a fluid. It is a measure of internal friction and is measured as the amount of tangential force exerted by one layer of fluid upon an adjacent layer as it driven across it at a given velocity. The viscosity of the fluid carrier has been found to affect conformability and flexibility of the present invention. The viscosity also affects the tendency for a dispersed powder phase change material to maintain its dispersion. For this reason, very low viscosity fluids, such as water and alcohol, are believed not to be desirable as carriers herein. Polydimethylsiloxane fluid and dimethicone fluid are more preferred for use herein.

Turning to FIG. 3, the body wrap 10 alternately includes a heat tube layer 35 for channeling heat from the warmer areas of the body wrap to the cooler areas. The heat tube layer 35 is made up of a number of attached heat tubes 36. The heat tube layer 35 preferably lies under and is insulated by the insulation layer 27, and is adjacent to the envelope 28, where it is close to the cold temperature of the phase change material. The heat tubes are preferably the same length and size as one another and are parallel to one another and connected together side by side. In one embodiment, the heat tubes include channels between heat tubes for the refrigerant to flow back and forth between heat tubes.

In a less preferred embodiment, at least one hollow heat tube 36, and preferably all of the heat tubes, holds a small amount of a refrigerant liquid 37, as shown in FIG. 3. The refrigerant liquid 37 has a boiling point between about 0 and 20 degrees Centigrade. Each heat tube contains only a small amount of the refrigerant liquid; sufficient empty space remains in each heat tube for expansion of the refrigerant liquid. The heat tube layer is enclosed, so that the refrigerant 37 does not escape from the heat tube layer 35.

The heat tubes are made of a flexible material, so that they are comfortable to sit or lie on. The heat tube material must be strong and able to contain the refrigerant and withstand the liquid to gas expansion. The heat tubes are preferably substantially made of a gas impermeable film.

Figure 4:
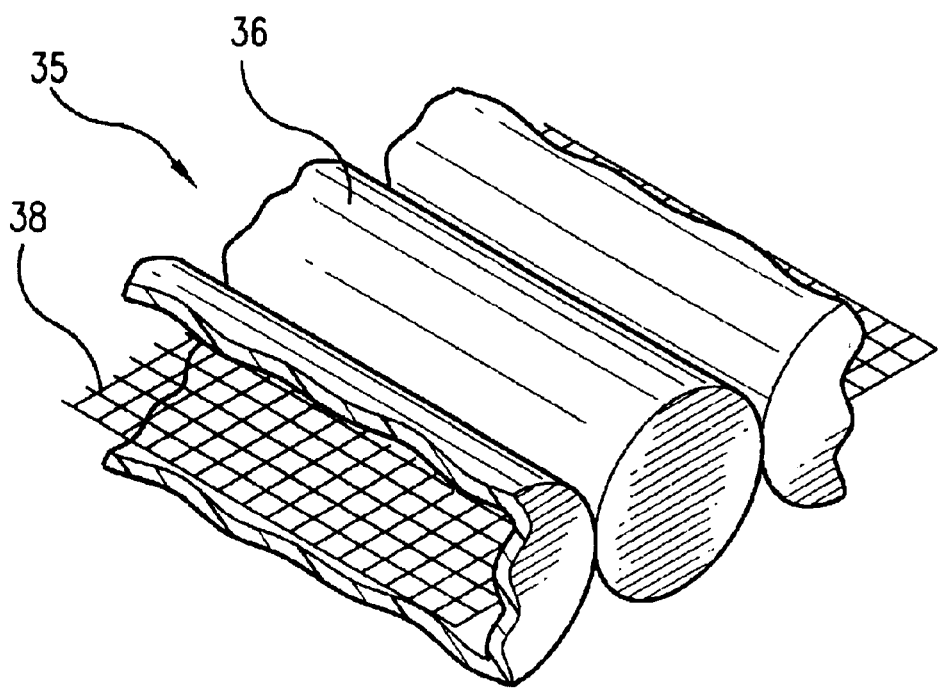
FIG. 4 is a partial cut-away perspective view of a heat tube layer of a body wrap according to the present invention.

Referring to FIG. 4, an optional ingredient in each heat tube is a thin, three-dimensional floating net 38, which preferably extends the length and width of the heat tube 36. The net 38 has small squares, which help to keep the heat tubes open despite pressure from the body or other weight on the support surface. The nets also help to distribute the refrigerant liquid 37 evenly in the heat tube 36. A helical spring type net or tubular net is preferred. The size of the spacing between the net strands is dictated in part by the diameter of the heat tube. Preferably, the heat tubes are made of vinyl, rubber, plastic, urethane, or an elastic polymer.

It has been found herein that one problem with some of the heat tube materials is that they crackle when a user sits or lies on them. In all embodiments herein, the heat tubes 36 may be surrounded by a second gel or viscous fluid, such as a silicone gel, and enclosed by a second envelope. The fluid/gel muffles the distracting crackling sound. This second envelope preferably lies side by side with the first, PCM-containing envelope 28. Another alternative is to include the heat tubes 36 in the PCM-containing envelope 28. The carrier 30 around the heat tubes 36 in the envelope 28 then muffles the crackling sound.

From the foregoing it can be realized that the described cooling body wrap of the present invention may be easily and conveniently utilized. It is to be understood that any dimensions given herein are illustrative, and are not meant to be limiting.

While preferred embodiments of the invention have been described using specific terms, this description is for illustrative purposes only. It will be apparent to those of ordinary skill in the art that various modifications, substitutions, omissions, and changes may be made without departing from the spirit or scope of the invention, and that such are intended to be within the scope of the present invention as defined by the following claims. It is intended that the doctrine of equivalents be relied upon to determine the fair scope of these claims in connection with any other person's product which fall outside the literal wording of these claims, but which in reality do not materially depart from this invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

LIST OF REFERENCE NUMBERS USED IN THE DRAWINGS 10 body wrap
11 torso body wrap
12 head body wrap
13 outside face
14 inside face
15 fastening means
16 first fastening members
17 second fastening members
18 first side of torso body wrap
19 cutout in head body wrap
20 left neck flap of head body wrap
21 right neck flap of head body wrap
22 second side of body wrap
23 top edge of body wrap
24 bottom edge of body wrap
26 outer protective layer
27 insulation layer
28 envelope
29 inner layer
30 carrier
31 phase change material
32 temperature indicator window
33 thermometer
35 heat tube layer
36 heat tube
37 refrigerant
38 net in heat tube

What is claimed is:

1. A body wrap for rapidly cooling a part of the body, comprising
   (a) a phase change material having a melting point of between about −10 and 6 degrees Centigrade;
   (b) a gel or viscous fluid carrier in which the phase change material is substantially evenly distributed;
   (c) a fluid-impermeable, conformable, sealed envelope surrounding the phase change material and the carrier;
   (d) at least one layer of insulation adjacent to a first side of the envelope;
   (e) a fastener means for removably fastening the body wrap around a part of the body; and
   (f) a heat tube layer adjacent to an opposite, second side of the envelope, the heat tube layer being comprised of a plurality of heat tubes connected to one another.

2. A body wrap according to claim 1, wherein the envelope is a urethane film.

3. A body wrap according to claim 2, wherein the fastener means is strips of hook and loop attached along one side of the body wrap.

4. A body wrap according to claim 2, wherein the phase change material is microencapsulated with a polymer coating, forming generally spherical PCM/polymer microcapsules which range in diameter between about one and about 100 microns.

5. A body wrap according to claim 2, wherein the carrier is a silicone fluid.

6. A body wrap according to claim 1, wherein the carrier is an oil.

7. A body wrap according to claim 1, wherein the carrier is urethane gel.

8. A body wrap according to claim 1 wherein the phase change material is a C12 to C14 alkane, or a combination thereof.

9. A body wrap according to claim 1, wherein the body wrap is rollable and insertable in a cooler for transport.

10. A body wrap according to claim 1, wherein at least one of the heat tubes contains a refrigerant liquid with a boiling point between about 0 and about 20 degrees Centigrade.

11. A body wrap for rapidly inducing hypothermia, comprising
    (a) a fluid-impermeable, flexible, conformable envelope;
    (b) a mixture of from about 10 to about 75 weight % of alkanes having a carbon chain length of between 10 and 14 and from about 25 to about 90 weight % of a gel or viscous fluid carrier in which the alkanes are substantially evenly distributed, the mixture being sealed within the envelope;
    (c) at least one layer of insulation adjacent to a first side of the envelope;
    (d) a fastening means for fastening the body wrap around a part of the body; and
    (e) a heat tube layer adjacent to a second, opposite side of the envelope, the heat tube layer being comprised of a plurality of heat tubes connected to one another.

12. A body wrap according to claim 11, wherein the alkane is microencapsulated with a polymer coating, forming generally spherical microcapsules ranging in diameter between about one and about 100 microns.

13. A support surface according to claim 11, further comprising a net suspended within at least one of the heat tubes.

14. A body wrap according to claim 1, which does not comprise a power source or microprocessor.

15. A body wrap according to claim 11, wherein the envelope is a urethane film.

16. A body wrap according to claim 11, wherein the carrier is a mineral oil, a silicone fluid, or a urethane gel.

17. A body wrap according to claim 15, further comprising an outer protective layer adjacent to an outer side of the insulation layer, and an inner, conformable layer adjacent to an opposite side of the envelope.

18. A body wrap according to claim 11, wherein the alkane is dodecane, tridecane, tetradecane, or a mixture thereof.

19. A cooling body wrap for rapidly inducing hypothermia, comprising:

(a) a fluid-impermeable, flexible, conformable envelope;

(b) a mixture of from about 10 to about 75 weight % of alkanes having a carbon chain length of between 10 and 14 and from about 25 to about 90 weight % of a gel or viscous fluid carrier in which the alkanes are substantially evenly distributed, the mixture being sealed within the envelope;

(c) at least one layer of insulation adjacent to a first side of the envelope;

(d) a fastening means for fastening the body wrap around a part of the body; and further comprising at least two adjacent heat tubes within the envelope, at least one of the heat tubes containing a refrigerant liquid.

20. A cooling body wrap for rapidly inducing hypothermia, comprising:

(a) a fluid-impermeable, flexible, conformable envelope;

(b) a mixture of from about 10 to about 75 weight % of alkanes having a carbon chain length of between 10 and 14 and from about 25 to about 90 weight % of a gel or viscous fluid carrier in which the alkanes are substantially evenly distributed, the mixture being sealed within the envelope;

(c) at least one layer of insulation adjacent to a first side of the envelope;

(d) a fastening means for fastening the body wrap around a part of the body; and further comprising a plurality of heat tubes within a second, gel or viscous fluid-filled envelope, at least one of the heat tubes containing a refrigerant liquid with a boiling point between about 0 and about 20 degrees Centigrade.

* * * * *